(12) United States Patent
Sgroi, Jr.

(10) Patent No.: US 10,499,922 B2
(45) Date of Patent: Dec. 10, 2019

(54) STAPLING DEVICE WITH SELF-RELEASING KNIFE CARRIER PUSHER

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 225 days.

(21) Appl. No.: 15/797,216

(22) Filed: Oct. 30, 2017

(65) Prior Publication Data
US 2018/0125495 A1    May 10, 2018

Related U.S. Application Data

(60) Provisional application No. 62/417,537, filed on Nov. 4, 2016.

(51) Int. Cl.
  *A61B 17/115*  (2006.01)
  *A61B 17/072*  (2006.01)
  *A61B 17/00*   (2006.01)

(52) U.S. Cl.
  CPC .... *A61B 17/1155* (2013.01); *A61B 17/07207* (2013.01); *A61B 2017/00473* (2013.01); *A61B 2017/07257* (2013.01); *A61B 2017/07271* (2013.01); *A61B 2017/07285* (2013.01)

(58) Field of Classification Search
  CPC .......... A61B 17/1155; A61B 17/07207; A61B 2017/00473; A61B 2017/07257; A61B 2017/07285; A61B 2017/07271
  See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| CA | 908529 A | 8/1972 |
|---|---|---|
| CA | 2805365 A1 | 8/2013 |

(Continued)

*Primary Examiner* — Andrew M Tecco (57) ABSTRACT

A circular stapling device includes a reload and an elongate body or adaptor. The reload includes a staple pusher assembly, a knife carrier, and an annular knife supported on the knife carrier. The adaptor includes a pusher drive member and a knife carrier pusher having at least one resilient finger that is deformable inwardly towards the knife carrier into releasable engagement with the knife carrier to releasably couple the knife carrier to the knife carrier pusher. In a pre-fired state, the pusher is positioned to retain the resilient finger in the deformed state to prevent separation of the knife carrier pusher and the knife carrier. After the stapling device is fired and the knife carrier is advanced and subsequently retracted, the resilient finger of the knife carrier pusher is positioned to flex outwardly from the deformed state to automatically uncouple the knife carrier pusher from the knife carrier.

15 Claims, 8 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A * | 3/1985 | Filipi .................. A61B 17/115 227/155 |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A * | 9/1990 | Lipatov ................ A61B 17/115 227/180.1 |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |

(56) References Cited

U.S. PATENT DOCUMENTS

| | | |
|---|---|---|
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | |
|---|---|---|
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,750,503 B2 * | 9/2017 | Milliman ............... A61B 90/98 |
| 10,178,994 B2 * | 1/2019 | Lee .................... A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |

(56) References Cited

U.S. PATENT DOCUMENTS

| | | |
|---|---|---|
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0000428 A1* | 1/2016 | Scirica .................. A61B 50/30 227/180.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |

* cited by examiner

STAPLING DEVICE WITH SELF-RELEASING KNIFE CARRIER PUSHER

CROSS-REFERENCE TO RELATED APPLICATIONS

This application claims the benefit of and priority to U.S. Provisional Patent Application No. 62/417,537 filed Nov. 4, 2016, the entire disclosure of which is incorporated by reference herein.

BACKGROUND

1. Technical Description

The present disclosure is directed to circular stapling devices and, more particularly, to circular stapling devices including self-releasing knife carrier pushers.

2. Background of Related Art

Known circular stapling devices, including many powered stapling devices, have separate stapling and cutting functions. In such circular stapling devices, after staples have been fired from a shell assembly or reload of the stapling device, a knife carrier pusher engaged with a knife carrier is advanced to advance a knife supported on the knife carrier to cut tissue. The knife carrier pusher can be a component of an adaptor of the circular stapling device and the knife carrier and the knife can be components of the reload of the circular stapling device. In some current designs, a back angle on the knife carrier pusher is used to cam the knife carrier pusher from engagement with the knife carrier to facilitate removal of the reload from the stapling device. However, in these designs, if the back angle selected is too small, the knife carrier can be damaged upon removal of the reload from the adaptor. In addition, if the angle selected is too large, disengagement of the knife carrier pusher from the knife carrier can occur prematurely such that full retraction of the knife is not achieved.

A need exists in the stapling arts for a circular stapler that has a simple, reliable mechanism to effect engagement and disengagement of the knife carrier and the knife carrier pusher.

SUMMARY

In one aspect of the disclosure, a surgical stapling device includes a handle assembly, an adaptor supported on the handle assembly, and a reload. The adaptor includes a pusher driver and a knife carrier pusher. The knife carrier pusher defines a longitudinal axis and includes a body and at least one resilient finger. The at least one resilient finger has a proximal portion pivotally connected to the body and a distal portion including first engagement structure. The at least one resilient finger is pivotal between a first position diverging outwardly from the longitudinal axis and a second position pivoted inwardly of the first position. The reload is releasably coupled to a distal portion of the adaptor and includes a housing, a staple cartridge supported on a distal end of the housing, staples supported within the staple cartridge, a staple pusher defining a through bore, a knife carrier movably positioned within the through bore of the staple pusher, and an annular knife supported on the knife carrier. The knife carrier includes second engagement structure configured to releasably engage the first engagement structure of the at least one resilient finger to releasably couple the knife carrier to the knife carrier pusher. The pusher driver is movable from a retracted position to an advanced position to move the staple pusher within the housing to eject the staples from within the staple cartridge. The staple pusher, in a pre-fired state, is positioned to retain the at least one resilient finger of the knife carrier pusher in engagement with the knife carrier, and, in a fired state, is positioned to allow the at least one resilient finger to pivot to the second position to uncouple the knife carrier pusher from the knife carrier.

In embodiments, the first and second engagement structures of the knife carrier and the knife carrier pusher are positioned within the through bore of the staple pusher when the staple pusher is in a pre-fired state.

In some embodiments, the first engagement structure includes an annular channel formed about the knife carrier pusher.

In certain embodiments, the second engagement structure includes a detent formed on the at least one resilient finger, wherein the detent is configured to be received within the annular channel to releasably couple the knife carrier to the knife carrier pusher.

In embodiments, the pusher driver is positioned to abut the staple pusher such that distal movement of the pusher driver effects distal movement of the staple pusher.

In some embodiments, the pusher driver is movable proximally independently of the staple pusher.

In certain embodiments, the at least one resilient finger is connected to the body of the knife carrier pusher by a living hinge.

In embodiments, the at least one resilient finger includes a plurality of resilient fingers.

In some embodiments, in the second position of the plurality of resilient fingers, the plurality of resilient fingers defines a bore dimensioned to receive a proximal end of the knife carrier.

In certain embodiments, the proximal end of the knife carrier includes a tapered surface configured to facilitate passage of the proximal end of the knife carrier into a distal end of the bore of the knife carrier pusher when the knife carrier pusher is in the second position.

In embodiments, a proximal portion of the knife carrier defines a plurality of longitudinal slots, wherein the longitudinal slots are configured to allow the proximal portion of the knife carrier to flex inwardly to facilitate passage of the proximal end of the knife carrier into the distal end of the bore of the knife carrier pusher.

In some embodiments, the surgical stapling device is a powered surgical stapling device and the elongate body includes an adaptor.

In certain embodiments, the adaptor is releasably coupled to the handle assembly.

BRIEF DESCRIPTION OF THE DRAWINGS

Various embodiments of the presently disclosed surgical stapling device including a self-releasing knife carrier pusher are described herein below with reference to the drawings, wherein.

DETAILED DESCRIPTION OF EMBODIMENTS

The presently disclosed circular stapling device will now be described in detail with reference to the drawings in which like reference numerals designate identical or corresponding elements in each of the several views. In this description, the term "proximal" is used generally to refer to that portion of the stapling device that is closer to a clinician, while the term "distal" is used generally to refer to that portion of the stapling device that is farther from the clinician. In addition, the term "endoscopic" is used generally to refer to endoscopic, laparoscopic, arthroscopic, and any other surgical procedure performed through a small incision or a cannula inserted into a patient's body. Finally, the term clinician is used generally to refer to medical personnel including doctors, surgeons, nurses, and support personnel.

The presently disclosed circular stapling device includes a shell assembly or reload and an adaptor. The reload includes a staple cartridge that supports a plurality of annular rows of staples, a staple pusher assembly, a knife carrier, and an annular knife supported on the knife carrier. The adaptor includes, inter alia, a pusher drive member and a knife carrier pusher. The knife carrier pusher includes a plurality of resilient fingers that are deformable inwardly towards the knife carrier into releasable engagement with the knife carrier. In a pre-fired state, the pusher is positioned to retain the plurality of fingers in the deformed state to retain the knife carrier pusher and the knife carrier in engagement. After the stapling device is fired and the knife carrier is advanced and subsequently retracted, the engaging surfaces of the knife carrier and knife carrier pusher are positioned proximally of staple pusher assembly such that the staple pusher assembly is no longer positioned to retain the knife carrier pusher and the knife carrier in engagement. Thus, when the knife carrier pusher and the knife carrier are retracted to a position proximal of the staple pusher assembly, the plurality of resilient fingers of the knife carrier pusher flex outwardly from the deformed state out of engagement with the knife carrier to automatically disengage from the knife carrier. A cam action is not required to effect uncoupling of the knife carrier and the knife carrier pusher.

Figure 1:
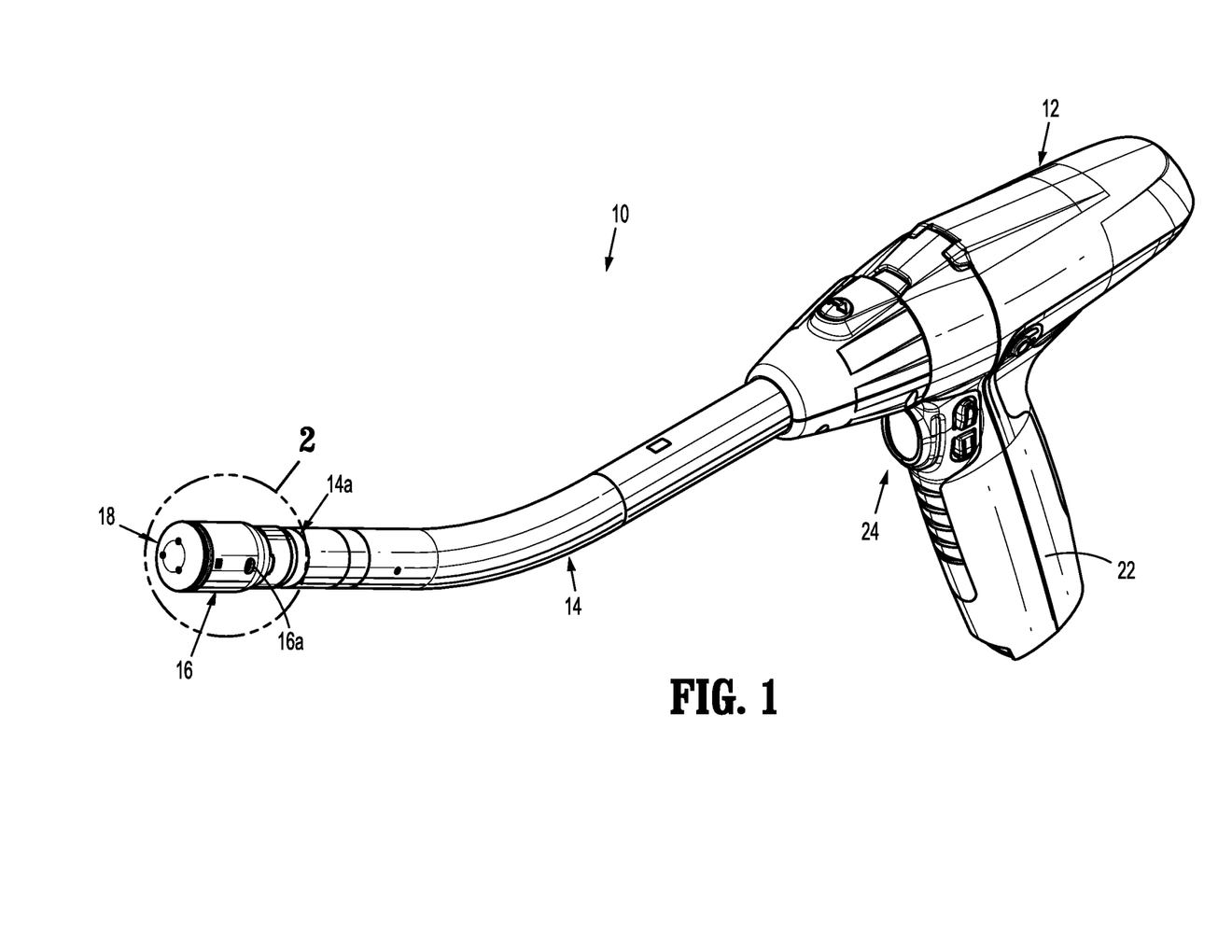
FIG. 1 is a side perspective view an exemplary embodiment of the presently disclosed circular stapling device.
Figure 2:
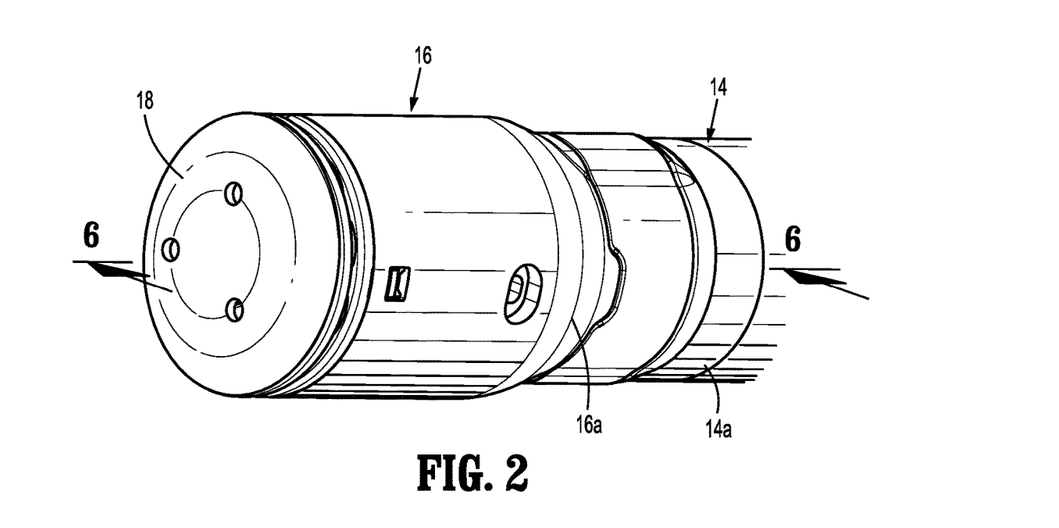
FIG. 2 is an enlarged view of the indicated area of detail shown in FIG. 1.

FIGS. 1 and 2 illustrate an exemplary embodiment of the presently disclosed powered surgical stapling device 10. Although illustrated as a powered surgical stapling device, it is envisioned that the stapling device 10 can be configured for manual actuation. The stapling device 10 includes a handle assembly 12, an elongate body or adaptor assembly 14, a reload 16, and anvil assembly 18 supported for movement in relation to the reload 16 between spaced and approximated positions as is known in the art. The reload 12 includes a proximal end 16a that is releasably coupled to a distal end 14a of the adaptor assembly 14. The handle assembly 12 includes a stationary grip 22, and actuation buttons 24 for controlling operation of the various functions of the stapling device including approximation of the reload and anvil assemblies 16, 18, firing of staples (not shown) from the reload 16, and cutting of tissue. The adaptor 14 is coupled to the handle assembly 12 to translate power from the handle assembly 12 to the reload and anvil assemblies 16, 18. U.S. Pat. No. 9,023,014 ("the '014 patent"), and U.S. Pat. No. 9,055,943 ("the '943 patent) disclose examples of surgical stapling devices including exemplary powered handle assemblies. Each of these patents is incorporated herein by reference in its entirety.

Figure 3:
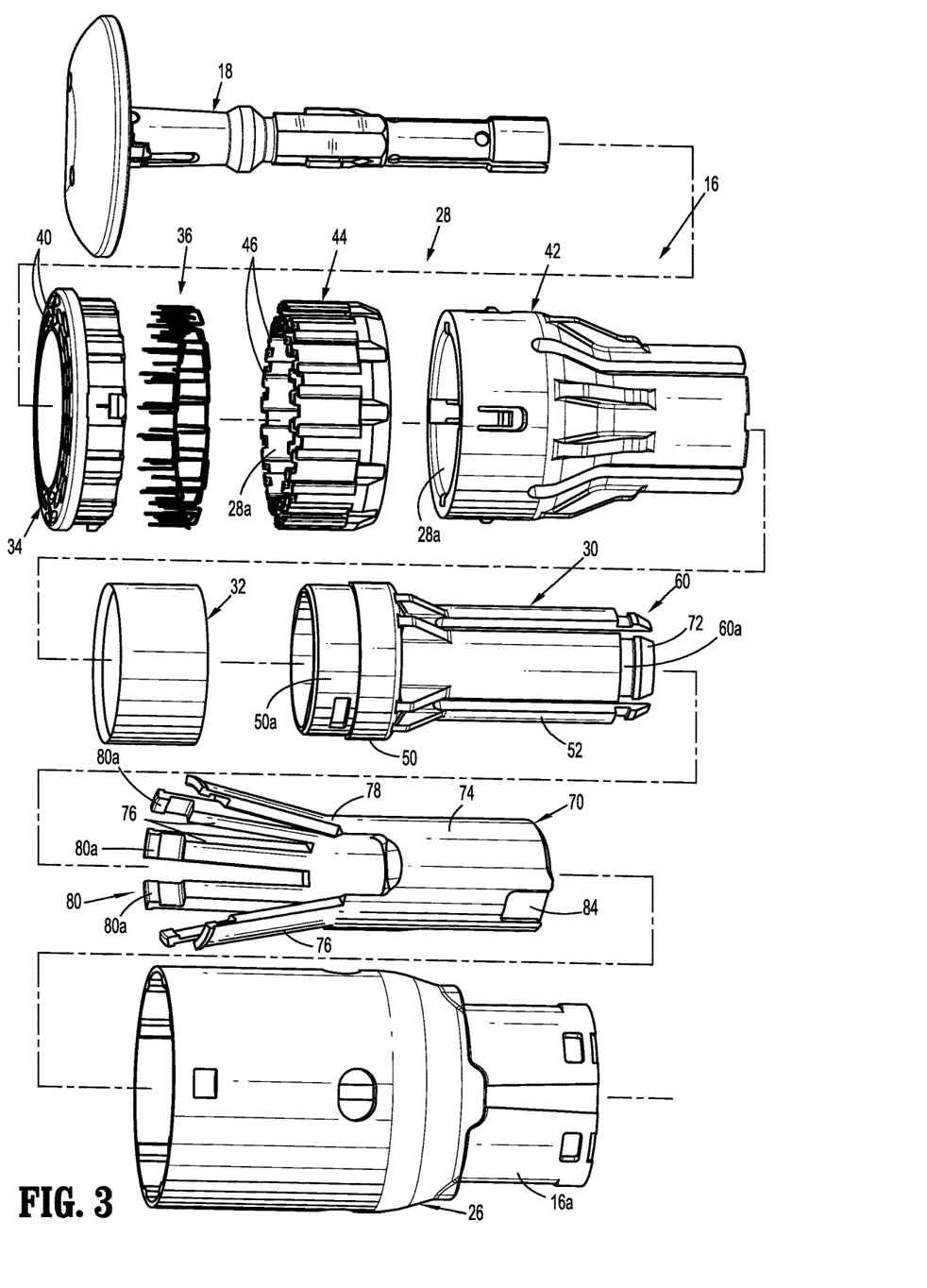
FIG. 3 is a side, perspective, exploded view of the reload of the circular stapler shown in FIG. 2.

Referring to FIG. 3, the reload 16 includes a housing 26, a pusher assembly 28, a knife carrier 30, an annular knife 32 supported on the knife carrier 30, a staple cartridge 34, and staples 36 supported within the staple cartridge 34. The staple cartridge 34 defines annular rows of staple pockets 40. Each of the staple pockets 40 supports one of the staples 36. The pusher assembly 28 includes an annular pusher back 42 and a staple pushing member 44 that together define a longitudinal through bore 28a. The pusher back 42 has a distal end that engages a proximal end of the staple pushing member 44 such that distal movement of the pusher back 42 within the housing 26 effects distal movement of the staple pushing member 44 within the housing 26. The staple pushing member 44 of the reload 16 has a plurality of fingers 46. Each of the plurality of fingers 46 is received within a respective one of the staple pockets 40 of the staple cartridge 34 and is movable through the staple pocket 40 to eject the staple 36 from the staple pocket 40 when the staple pushing member 44 is moved distally within the housing 26 from a retracted position to an advanced position.

Figure 4:
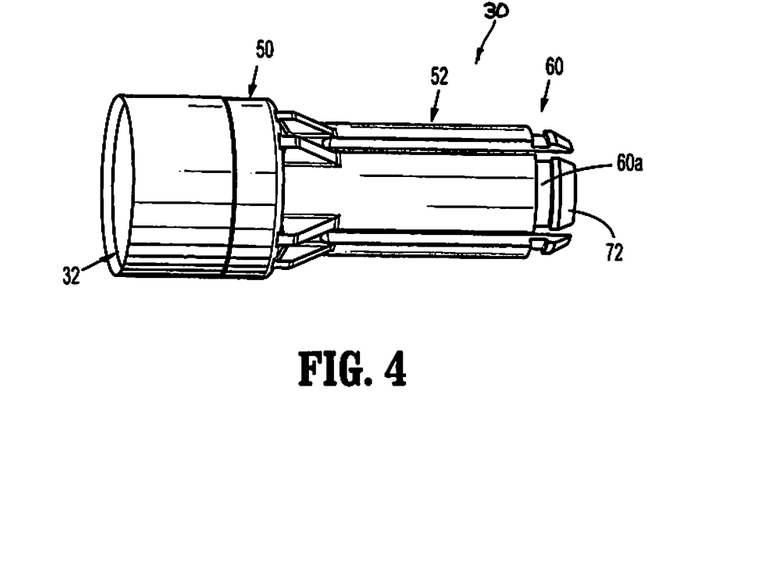
FIG. 4 is a side, perspective view of the knife carrier of a reload of the circular stapling device shown in FIG. 2.

Referring also to FIG. 4, the knife carrier 30 is movably supported within the through bore 28a of the pusher assembly 28 and includes a substantially cylindrical distal portion 50 and a substantially cylindrical smaller diameter proximal portion 52. The smaller diameter proximal portion 52 includes a plurality of longitudinal slots 54 that receive projections (not shown) defined within the pusher back 42 to guide movement of the knife carrier 30 from a retracted position to an advanced position within the pusher assembly 28. The longitudinal slots 54 also facilitate inward flexing of the proximal portion 52 of the knife carrier 30 as discussed in further detail below. The knife 32 is secured about the distal portion 50 of the knife carrier 30 such as by crimping. Alternately, other fastening techniques can be used to secure the knife 32 to the knife carrier 30. In embodiments, a distal portion 50a of the distal portion 50 is recessed to receive the annular knife 32.

The proximal portion 52 of the knife carrier 30 defines first engagement structure 60 that is configured to engage a distal end of a knife carrier pusher 70 of the adaptor 14 as described below to releasably couple the knife carrier 30 to the knife carrier pusher 70. In embodiments, the first engagement structure 60 includes an annular channel 60a. The annular channel 60a is configured to receive second engagement structure 80 formed on a distal end of the knife carrier pusher 70 as described in further detail below. In embodiments, a proximal end 72 of the proximal portion 52 of the knife carrier 30 is tapered inwardly in the proximal direction. The tapered proximal end 72 and the longitudinal slots 54 of the knife carrier 30 facilitate attachment of the knife carrier 30 to the knife carrier pusher 70 when the knife carrier pusher 70 is in a deformed state as described in detail below.

Figure 5:
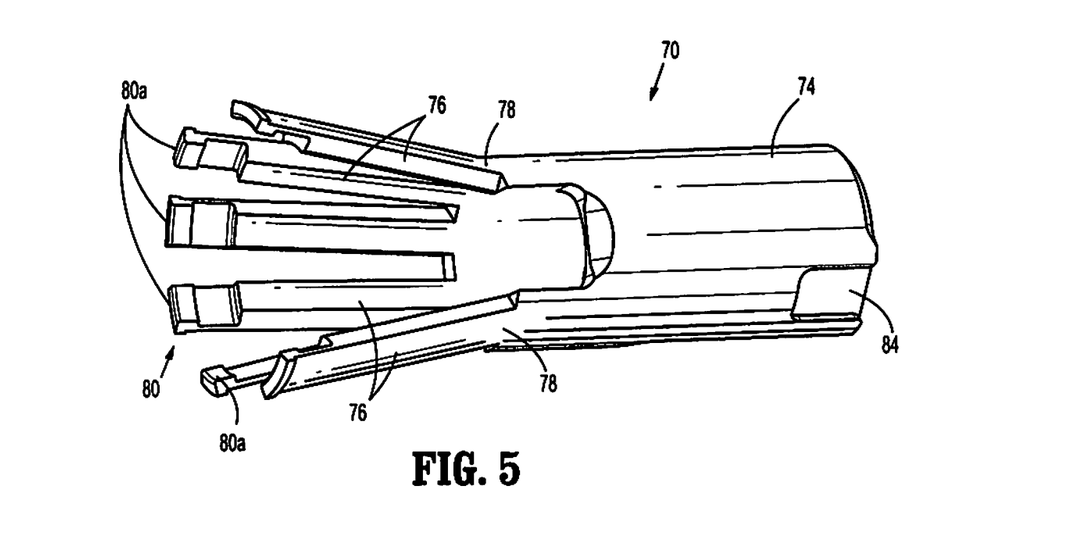
FIG. 5 is a side, perspective view of a knife carrier pusher of the circular stapling device shown in FIG. 1.
Figure 6:
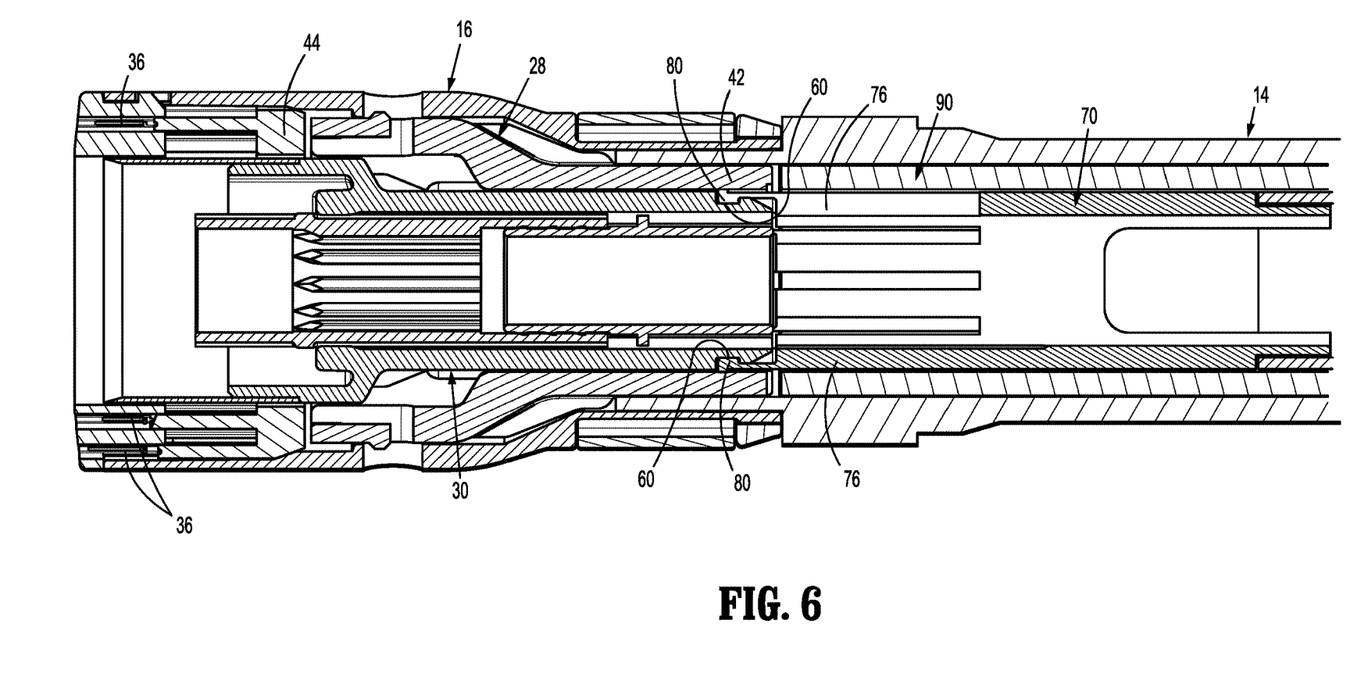
FIG. 6 is a side cross-sectional view taken along section line 6-6 of FIG. 2 in a pre-fired state.

Referring also to FIG. 5, the knife carrier pusher 70 includes an annular body portion 74 defining a longitudinal axis and a plurality resilient spring fingers 76 extending distally from the body portion 74. In embodiments, the spring fingers 76 have a first end connected to the body portion 74 by a living hinge 78. Alternately, the spring fingers 76 may be formed of a substantially rigid material and connected to the body portion 74 by pivot pins (not shown) and urged outwardly by a biasing member (not shown). The spring fingers 76 define an axis that diverges outwardly from the longitudinal axis of the body portion 74 in the distal direction when the spring fingers 76 are in a non-deformed state and define an axis that is substantially parallel to the longitudinal axis of the body portion 74 when the spring fingers 76 are deformed or urged inwardly about the living hinge 78. In the inwardly deformed state, the fingers 76 define a bore 76a (FIG. 6). The distal end of each of the spring fingers 76 includes the second engagement structure 80. In embodiments, the second engagement structure 80 includes a protrusion 80a that is received within the annular channel 60a when the spring fingers 76 are in the deformed state.

The body portion 74 defines recesses 84 that are configured to engage a drive member (not shown) supported within the adaptor 14. The drive member is secured to the proximal end of the knife carrier pusher 70 and is operable to advance and retract the knife carrier pusher 70 within the housing 26 of the reload 16 as known in the art. U.S. Publication No. 2016/0106406 ("the '406 Publication") which was filed on Oct. 6, 2015 discloses such an adaptor and is incorporated herein in its entirety by reference.

Referring to FIG. 6, the adaptor 14 also includes a pusher drive member 90. The pusher drive member 90 has a distal end that abuts the proximal end of the pusher back 42 of the pusher assembly 28 such that distal movement of the pusher drive member 90 effects distal movement of the pusher assembly 28 including the pusher back 42 and the staple pushing member 44. The pusher drive member 90 is not coupled to the pusher assembly 28. Thus, proximal movement of the pusher drive member 90 does not affect proximal movement of the pusher assembly 28. The '406 Publication discloses an adaptor 14 including a pusher drive member and, as discussed above, is incorporated herein reference in its entirety.

FIG. 6 illustrates the stapling device 10 in a pre-fired state. In the pre-fired state, the pusher assembly 28 and the knife carrier 30 of the reload 16 are in a retracted position. In addition, the knife carrier pusher 70 and the pusher drive member 90 are in a retracted position. In the retracted position, the pusher assembly 28 and the pusher drive member 90 are positioned about the spring fingers 76 of the knife carrier pusher 70 to retain the spring fingers 76 in the inwardly deformed state. In the inwardly deformed state, the second engagement structure 80 on the spring fingers 76 is engaged with the first engagement structure 60 on the proximal end of the knife carrier pusher 70 to releasably couple the knife carrier pusher 70 to the knife carrier 30.

Figure 6A:
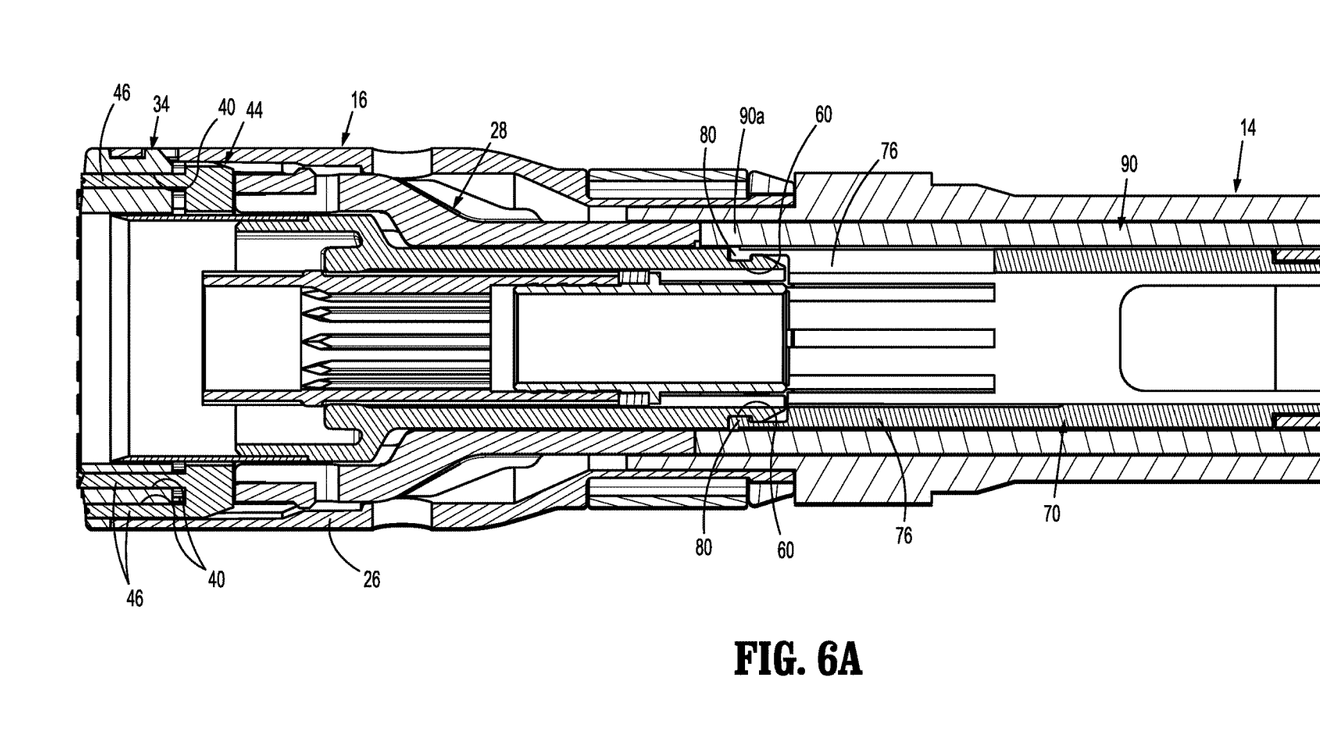
FIG. 6A is a side cross-sectional view taken along section line 6-6 of FIG. 2 in a post-fired state prior to advancement of the knife.

Referring to FIG. 6A, when the powered handle assembly 12 (FIG. 1) is actuated to fire staples 36 (FIG. 6) from the staple cartridge 34, the pusher drive member 90 is advanced from a retracted position (FIG. 6) to an advanced position (FIG. 6A) to advance the pusher assembly 28 within the housing 26 of the reload 16. As the pusher assembly 28 is advanced distally within the housing 26 of the reload 16, the fingers 46 of the staple pushing member 44 move through the staple pockets 40 of the staple cartridge 34 to eject the staples 36 from the staple cartridge 34 into the anvil assembly 18 (FIG. 1). As this occurs, a distal end 90a of the pusher drive member 90 remains in contact with the spring fingers 76 of the knife carrier pusher 70 to maintain engagement between the first and second engagement structures 60, 80 to retain the knife carrier pusher 70 coupled to the knife carrier 30.

Figure 7:
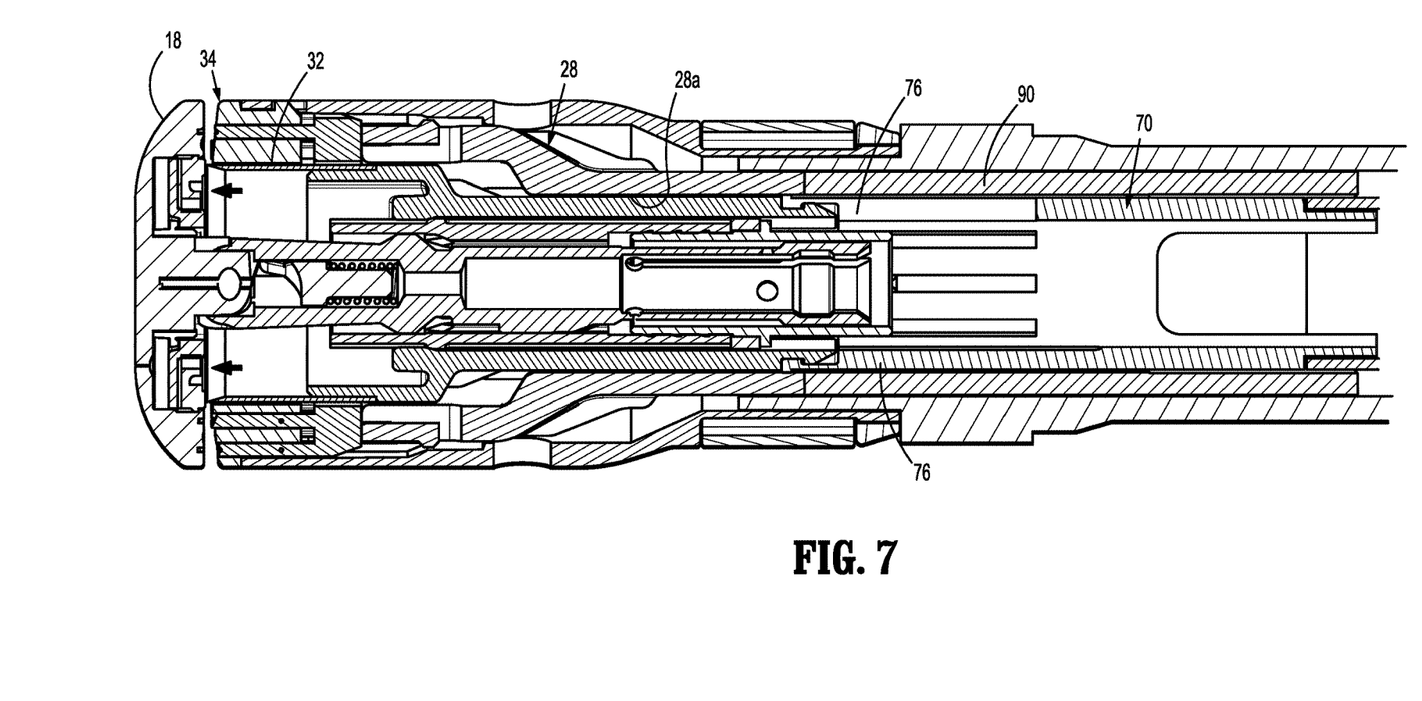
FIG. 7 is a side cross-sectional view taken along section line 6-6 of FIG. 2 in a post-fired state as the knife is advanced.

Referring to FIG. 7, when the powered handle 12 (FIG. 1) is actuated to cut tissue, the knife carrier pusher 70 is advanced from its retracted position to its distal position to advance the knife carrier 30 distally within the through bore 28a of the pusher assembly 28. As the knife carrier 30 is advanced, the knife 32 which is secured to the knife carrier 30 is advanced towards the anvil assembly 18 to cut or transect tissue clamped between the anvil assembly 18 and the staple cartridge 34 of the reload 16. As shown, when the knife carrier 30 and knife carrier pusher 70 are advanced distally within the pusher assembly 28, the spring fingers 76 are confined within the through bore 28a of the pusher assembly 28 and a through bore 100 defined by the pusher drive member 90 and, thus, remain in engagement with the proximal end of the knife carrier 30.

Figure 8:
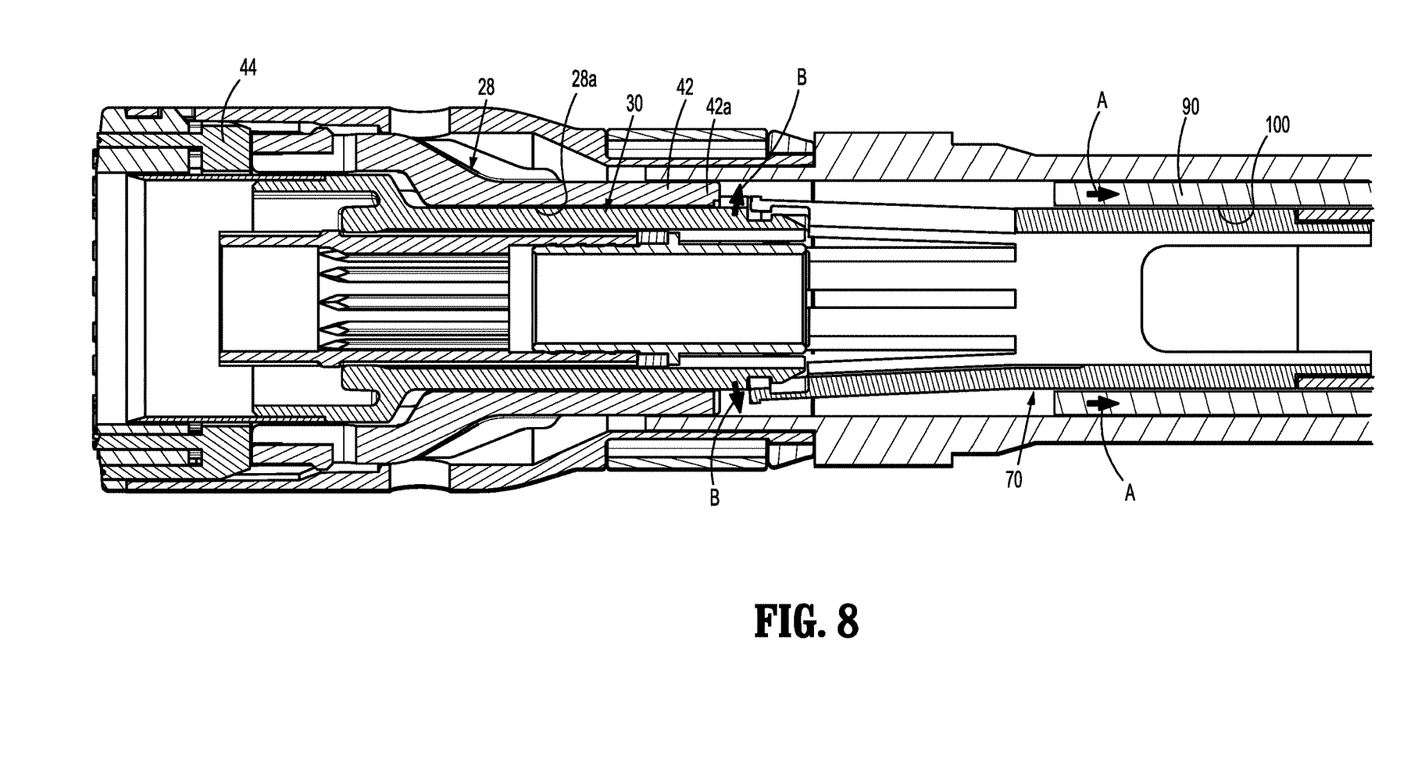
FIG. 8 is a side cross-sectional view taken along section line 6-6 of FIG. 2 in a post-fired state after advancement of the knife with the pusher driver retracted and the knife carrier and knife carrier pusher retracted.

Referring to FIG. 8, when the powered handle 12 (FIG. 1) is actuated to retract the pusher drive member 90 in a direction indicated by arrows "A", the pusher assembly 28, including the pusher back 42 and the staple pushing member 44, remains in its advanced position. More specifically, since the pusher drive member 90 only abuts but is not coupled to the pusher assembly 28, the pusher assembly 28 is not retracted with the pusher drive member 90 and remains in its advanced position when the pusher drive member 90 is retracted. When the knife carrier pusher 70 is retracted to retract the knife carrier 30 within the through bore 28a of the pusher assembly 28, the spring fingers 76 move to a position proximal of the proximal end 42a of the pusher back 42. When the spring fingers 76 are retracted to a position beyond the proximal end 42a of the pusher back 42, the spring fingers 76, due to their resilience, return to their non-deformed state in the direction indicated by arrows "B" and disengage from the knife carrier 30. More particularly, when the spring fingers 76 pass beyond the proximal end 42a of the pusher back 42, the spring fingers 76 spring outwardly to disengage the second engagement structure 80 from the first engagement structure 60 to uncouple the knife carrier 30 from the knife carrier pusher 70.

With the knife carrier 30 disengaged from the knife carrier pusher 70, the reload 16 can be uncoupled from the adaptor 14 to facilitate attachment of a new or fresh reload 16 to the adaptor 14. As used herein, the term "fresh" reload means a reload loaded with staples 36. In a fresh reload, the pusher assembly 28 is located in the proximal position as shown in FIG. 6. When the fresh reload 16 is loaded onto the adaptor 14, the pusher drive member 90 is advanced to a position to move the spring fingers 76 to the inwardly deformed position and the tapered ends 72 of the knife carrier 30 are inserted into the bore 76a (FIG. 6) defined by the spring fingers 76. When the tapered ends 72 engage the distal end of the knife carrier pusher 70, the proximal portion 52 is deformed inwardly to allow the first engagement structure 60 and the second engagement structure 80 to move into engagement to releasably couple the knife carrier 30 of the fresh reload 16 to the knife carrier pusher 70.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
   a handle assembly;
   an elongate body supported on the handle assembly, the elongate body including a pusher driver and a knife carrier pusher, the knife carrier pusher defining a longitudinal axis and including a body and at least one resilient finger, the at least one resilient finger having a proximal portion pivotally connected to the body and a distal portion including first engagement structure, wherein the at least one resilient finger is pivotal between a first position diverging outwardly from the longitudinal axis and a second position pivoted inwardly of the first position; and
   a reload releasably coupled to a distal portion of the elongate body, the reload including a housing, a staple cartridge supported on a distal end of the housing, staples supported within the staple cartridge, a staple pusher defining a through bore, a knife carrier movably positioned within the through bore of the staple pusher, and an annular knife supported on the knife carrier, the knife carrier including second engagement structure configured to releasably engage the first engagement structure to releasably couple the knife carrier to the knife carrier pusher, wherein the pusher driver is movable from a retracted position to an advanced position to move the staple pusher within the housing to eject the staples from within the staple cartridge, the staple pusher, in a pre-fired state being positioned to retain the at least one resilient finger of the knife carrier pusher in engagement with the knife carrier, and, in a fired state, being positioned to allow the at least one resilient finger to pivot to the second position to uncouple the knife carrier pusher from the knife carrier.

2. The surgical stapling device of claim 1, wherein the first and second engagement structures of the knife carrier and the knife carrier pusher are positioned within the through bore of the staple pusher when the staple pusher is in the pre-fired state.

3. The surgical stapling device of claim 2, wherein the first engagement structure includes an annular channel formed about the knife carrier pusher.

4. The surgical stapling device of claim 3, wherein the second engagement structure includes a detent formed on the at least one resilient finger, the detent being configured to be received within the annular channel to releasably couple the knife carrier to the knife carrier pusher.

5. The surgical stapling device of claim 1, wherein the pusher driver is positioned to abut the staple pusher such that distal movement of the pusher driver effects distal movement of the staple pusher.

6. The surgical stapling device of claim 5, wherein the pusher driver is movable proximally independently of the staple pusher.

7. The surgical stapling device of claim 1, wherein the at least one resilient finger is connected to the body of the knife carrier pusher by a living hinge.

8. The surgical stapling device of claim 7, wherein the at least one resilient finger includes a plurality of resilient fingers.

9. The surgical stapling device of claim 8, wherein in the second position, the plurality of resilient fingers define a bore dimensioned to receive a proximal end of the knife carrier.

10. The surgical stapling device of claim 9, wherein the proximal end of the knife carrier includes a tapered surface configured to facilitate passage of the proximal end of the knife carrier into a distal end of the knife carrier pusher when the knife carrier pusher is in the second position.

11. The surgical stapling device of claim 10, wherein a proximal portion of the knife carrier defines a plurality of longitudinal slots, the longitudinal slots being configured to allow the proximal portion of the knife carrier to flex inwardly to facilitate passage of the proximal end of the knife carrier into the distal end of the knife carrier pusher.

12. The surgical stapling device of claim 1, wherein the handle assembly is powered.

13. The surgical stapling device of claim 12, wherein the adaptor is releasably coupled to the handle assembly.

14. The surgical stapling device of claim 1, wherein the surgical stapling device is powered and the elongate body includes an adaptor.

15. The surgical stapling device of claim 14, wherein the adaptor is releasably coupled to the handle assembly.

* * * * *